(12) United States Patent
Overney et al.

(10) Patent No.: US 7,498,568 B2
(45) Date of Patent: Mar. 3, 2009

(54) REAL-TIME ANALYSIS OF MASS SPECTROMETRY DATA FOR IDENTIFYING PEPTIDIC DATA OF INTEREST

(75) Inventors: Gregor T. Overney, San Jose, CA (US); Joseph Charles Roark, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 320 days.

(21) Appl. No.: 11/117,874

(22) Filed: Apr. 29, 2005

(65) Prior Publication Data

US 2006/0243900 A1 Nov. 2, 2006

(51) Int. Cl.
*H01J 49/00* (2006.01)
(52) U.S. Cl. .................. 250/282; 250/281
(58) Field of Classification Search ............. 250/282
See application file for complete search history.

(56) References Cited

U.S. PATENT DOCUMENTS

| | | | |
|---|---|---|---|
| 5,206,507 A * | 4/1993 | Kelley .................. 250/282 |
| 6,147,348 A | 11/2000 | Quarmby et al. |
| 6,723,983 B2 | 4/2004 | Holle |
| 6,788,414 B1 | 9/2004 | Yeung et al. |
| 6,822,223 B2 | 11/2004 | Davis |
| 6,940,065 B2 * | 9/2005 | Graber et al. ............. 250/282 |
| 2003/0036207 A1 | 2/2003 | Washburn et al. |
| 2003/0129760 A1 | 7/2003 | Aguilera et al. |
| 2004/0033591 A1 | 2/2004 | Lubman et al. |
| 2004/0070763 A1 | 4/2004 | Yeung et al. |
| 2004/0108452 A1 | 6/2004 | Graber et al. |
| 2004/0121477 A1 | 6/2004 | Thompson et al. |
| 2004/0172200 A1 | 9/2004 | Kearney et al. |
| 2004/0248317 A1 | 12/2004 | Swamy et al. |
| 2004/0251409 A1 | 12/2004 | Le Blanc et al. |
| 2005/0063864 A1 | 3/2005 | Sano et al. |

OTHER PUBLICATIONS

Banoub, Joseph, et al., "Characterization and de Novo Sequencing of Atlantic Salmon Vitellogenin Protein by Electrospray Tandem and Matrix-assisted Laser Desorption/Ionization Mass Spectrometry," European Journal of Mass Spectrometry, vol. 10, No. 1, 2004, pp. 121-134.

(Continued)

*Primary Examiner*—David A. Vanore (57) ABSTRACT

A mass spectrometry system is described. The mass spectrometry system comprises: (a) a mass spectrometer; and (b) a controller connected to the mass spectrometer. The controller is configured to: (i) direct the mass spectrometer to acquire a precursor ion spectrum of a sample stream; (ii) analyze, in real-time, the precursor ion spectrum to determine whether a first evaluation criterion is satisfied; (iii) if the first evaluation criterion is satisfied, direct the mass spectrometer to acquire a product ion spectrum of the sample stream; (iv) analyze, in real-time, the product ion spectrum to determine whether a second evaluation criterion is satisfied; and (v) if the second evaluation criterion is satisfied, analyze the product ion spectrum to assign an identification to the product ion spectrum. For certain implementations, the controller allows automated, data-dependent acquisition of mass spectrometry data to improve the efficiency at which peptidic data of interest can be acquired.

24 Claims, 4 Drawing Sheets

OTHER PUBLICATIONS

Moehring, Thomas, et al., "Top-down Identification of Endogenous Peptides up to 9 kDA in Cerebrospinal Fluid and Brain Tissue by Nanoelectrospray Quadrupole Time-of-Flight Tandem Mass Spectrometry," Journal of Mass Spectrometry, vol. 40, No. 2, Feb. 2005, pp. 217-226.

Online document-IonSource.Com, "Peptide Sequence Tag," http://www.ionsource.com/tutorial/protID/peptidetag.htm, pp. 1-3, Mar. 8, 2005.

Online document-Applied Biosystems, "New Level of Confidence for Protein Identification: Results Dependent Analysis and Pepetide Mass Fingerprinting Using the 4700 Proteomics Discovery System," www.appliedbiosystems.com, 6 pages, 2003.

Baldwin, et al.., "Protein Identification by Mass Spectrometry." *Molecular & Cellular Proteomics* 3.1, pp. 1-9, 2004.

Brock et al., "Accurate Mass Elimination for the Acceleration of Protein Identification by LC MALDI QFT-ICR MS," *Proceedings for the 52$^{nd}$ ASMS Conference on Mass Spectrometry and Allied Topics*, Nashville, Tennessee, 2 pages, May 23-27, 2004.

Lin, et al., "Large-scale protein identification using mass spectrometry," *Biochimica et Biophysica Acta*, 1646:1-10 (2003).

Miller, et al. "Overview of Spectrum Mill MS Proteomics Workbench" *Agilent Technologies*, 12 pages, Dec. 12, 2003.

Sauber, et al., "Identification of Proteins in Post-Mortem Human Brain Tissue Laser Microdissection/Pressure Catapult and Nano-LC/MS/MS," *Agilent Technologies*, 8 pages, May 31, 2004.

\* cited by examiner

REAL-TIME ANALYSIS OF MASS SPECTROMETRY DATA FOR IDENTIFYING PEPTIDIC DATA OF INTEREST

TECHNICAL FIELD

The technical field of the invention relates to analytical instruments and, in particular, to mass spectrometry.

BACKGROUND

Various analytical instruments can be used for analyzing peptides, proteins, and other biomolecules. Mass spectrometry has gained prominence because of its ability to handle a wide variety of biomolecules with high sensitivity and rapid throughput. For example, proteins can be identified via analysis of spectra acquired using a tandem mass spectrometer. In some instances, the proteins are initially digested using a proteolytic agent to produce a variety of peptides, and the peptides are then analyzed by the tandem mass spectrometer to acquire a series of spectra.

In some instances, a tandem mass spectrometer is coupled to a chromatography system to analyze biomolecules present in a sample stream. For example, successive eluting portions of the sample stream can flow from a chromatography column, such as a High Performance Liquid Chromatography ("HPLC") column, into the tandem mass spectrometer, and a series of spectra can be acquired from the eluting portions. While coupling of the tandem mass spectrometer to the chromatography system is desirable for a variety of reasons, such a configuration presents challenges in terms of efficiency at which mass spectrometry data can be acquired during a particular chromatography run. For example, based on analyzing a spectrum acquired from a particular eluting portion of a sample stream, it can be desirable to acquire additional spectra from that same eluting portion. However, the rate of elution of biomolecules present in the sample stream can be too fast for effective manual control of the tandem mass spectrometer. Also, it can be undesirable or impractical to interrupt a flow of the sample stream. In addition, there might be insufficient material for repeated analysis.

SUMMARY

The invention provides a mass spectrometry system. The mass spectrometry system comprises: (a) a mass spectrometer; and (b) a controller connected to the mass spectrometer. The controller is configured to: (i) direct the mass spectrometer to acquire a precursor ion spectrum of a sample stream; (ii) analyze, in real-time, the precursor ion spectrum to determine whether a first evaluation criterion is satisfied; (iii) if the first evaluation criterion is satisfied, direct the mass spectrometer to acquire a product ion spectrum of the sample stream; (iv) analyze, in real-time, the product ion spectrum to determine whether a second evaluation criterion is satisfied; and (v) if the second evaluation criterion is satisfied, analyze the product ion spectrum to assign an identification to the product ion spectrum.

The invention also provides a computer-readable medium. The computer-readable medium comprises executable instructions to: (a) perform a peptide mass fingerprint search for a precursor ion spectrum to select a set of mass-to-charge ratios associated with the precursor ion spectrum; (b) direct acquisition of a set of product ion spectra at the set of mass-to-charge ratios; (c) perform a sequence tag analysis for the set of product ion spectra to select at least one of the set of product ion spectra; and (d) analyze the at least one of the set of product ion spectra to assign an identification to the precursor ion spectrum.

The invention also provides a method of operating a mass spectrometry system. The method comprises: (a) acquiring a precursor ion spectrum of a sample stream; (b) analyzing the precursor ion spectrum to determine whether a peptide mass fingerprint score criterion is satisfied; and (c) if the peptide mass fingerprint score criterion is satisfied, acquiring a product ion spectrum of the sample stream.

Advantageously, embodiments of the invention allow for real-time analysis of mass spectrometry data, such that results of the real-time analysis can be the basis for initiating or refining additional analysis or for initiating or refining acquisition of additional mass spectrometry data. For some embodiments of the invention, real-time analysis of mass spectrometry data can be achieved using a set of evaluation criteria that serve to effectively filter out mass spectrometry data that are irrelevant or uninteresting. In such manner, valuable memory resources and processing time can be devoted to mass spectrometry data that are actually relevant or interesting.

Other aspects and embodiments of the invention are also contemplated. The foregoing summary and the following detailed description are not meant to restrict the invention to any particular embodiment but are merely meant to describe some embodiments of the invention.

BRIEF DESCRIPTION OF THE DRAWING

For a better understanding of the nature and objects of some embodiments of the invention, reference should be made to the following detailed description taken in conjunction with the accompanying drawings.

DETAILED DESCRIPTION

Definitions

The following definitions apply to some of the elements described with respect to some embodiments of the invention. These definitions may likewise be expanded upon herein.

As used herein, the singular terms "a," "an," and "the" comprise plural referents unless the context clearly dictates otherwise. Thus, for example, reference to a controller can comprise multiple controllers unless the context clearly dictates otherwise.

As used herein, the term "set" refers to a collection of one or more elements. Thus, for example, a set of mass-to-charge ratios can comprise a single mass-to-charge ratio or multiple mass-to-charge ratios. Elements of a set can also be referred to as members of the set. Elements of a set can be the same or different. In some instances, elements of a set can share one or more common characteristics.

As used herein, the term "biomolecule" refers to a molecule that can be present in a biological sample. Examples of biomolecules comprise peptides, proteins, oligosaccharides, polysaccharides, lipids, nucleic acids, metabolites, and the like.

As used herein, the term "biological sample" refers to a sample obtained from, derived from, excreted by, or secreted by an organism, such as an unicellular organism or a multicellular organism. Typically, a biological sample comprises a set of biomolecules, such as a set of peptides or a set of proteins. Examples of biological samples comprise blood; plasma; serum; urine; bile; cerebrospinal fluid; aqueous or vitreous humor; bodily secretions; fluids obtained from an abscess or other site of infection or inflammation; fluids obtained from a joint; portions of any tissue or organ; primary cells; cultured cells; and media conditioned by any cell, tissue, or organ. In some instances, biological samples can be subjected to preliminary processing or other sample preparation procedures. For example, biomolecules present in a biological sample can be subjected to cleavage or proteolysis using any of a variety of proteolytic agents, such as trypsin, endoprotease glu-C, cyanogen bromide, and the like. As another example, a biological sample can be subjected to a set of separation procedures, such as subcellular fractionation, one-dimensional electrophoresis, two-dimensional electrophoresis, HPLC, and the like.

As used herein, the term "protein" refers to a molecule comprising multiple amino acids that are linked together. Typically, a protein comprises more than 50 amino acids that are linked together via peptide bonds. Examples of amino acids comprise the 20 genetically encoded amino acids, which comprise Alanine (one-letter abbreviation: A), Arginine (one-letter abbreviation: R), Asparagine (one-letter abbreviation: N), Aspartic acid (one-letter abbreviation: D), Cysteine (one-letter abbreviation: C), Glutamine (one-letter abbreviation: Q), Glutamate (one-letter abbreviation: E), Glycine (one-letter abbreviation: G), Histidine (one-letter abbreviation: H), Isoleucine (one-letter abbreviation: I), Leucine (one-letter abbreviation: L), Lysine (one-letter abbreviation: K), Methionine (one-letter abbreviation: M), Phenylalanine (one-letter abbreviation: F), Proline (one-letter abbreviation: P), Serine (one-letter abbreviation: S), Threonine (one-letter abbreviation: T), Tryptophan (one-letter abbreviation: W), Tyrosine (one-letter abbreviation: Y), and Valine (one-letter abbreviation: V). Additional examples of amino acids comprise D-amino acids, modified amino acids, amino acid analogs, synthetically produced amino acids, and the like. A protein can be naturally occurring, recombinantly produced, or synthetically produced. In some instances, a protein can be subjected to a set of post-translational modifications, such as glycosylation, acetylation, phosphorylation, ubiquitination, and the like.

As used herein, the term "peptide" refers to a molecule comprising multiple amino acids that are linked together. Typically, a peptide comprises multiple amino acids that are linked together via peptide bonds. A peptide can be naturally occurring, recombinantly produced, or synthetically produced. In some instances, a set of peptides can be produced by subjecting a protein to cleavage or proteolysis. A peptide that is produced by cleavage or proteolysis typically comprises from 2 to 50 amino acids.

As used herein, the term "peptidic" refers to being associated with, being indicative of, or being related to a set of peptides. Thus, for example, peptidic data can comprise data that are associated with, indicative of, or related to a set of peptides.

As used herein, the term "real-time" refers to performing a set of operations, such that an output or a result of the set of operations is produced based on a particular timing constraint. While an operation is sometimes referred to herein as being performed in real-time, it is contemplated that an output of the operation can be produced with some detectable delay or latency. For example, an operation can be performed in real-time if an output of the operation is produced at a rate that is the same as or substantially the same as a rate at which an input of the operation is acquired. As another example, an operation can be performed in real-time if an output of the operation is produced within a particular upper limit of response time, such as within 1 second, within 0.1 second, within 0.01 second, or within 0.001 second. As a further example, an operation can be performed in real-time if an output of the operation is timely produced so as to be capable of affecting or controlling a process while it is occurring.

Figure 1:
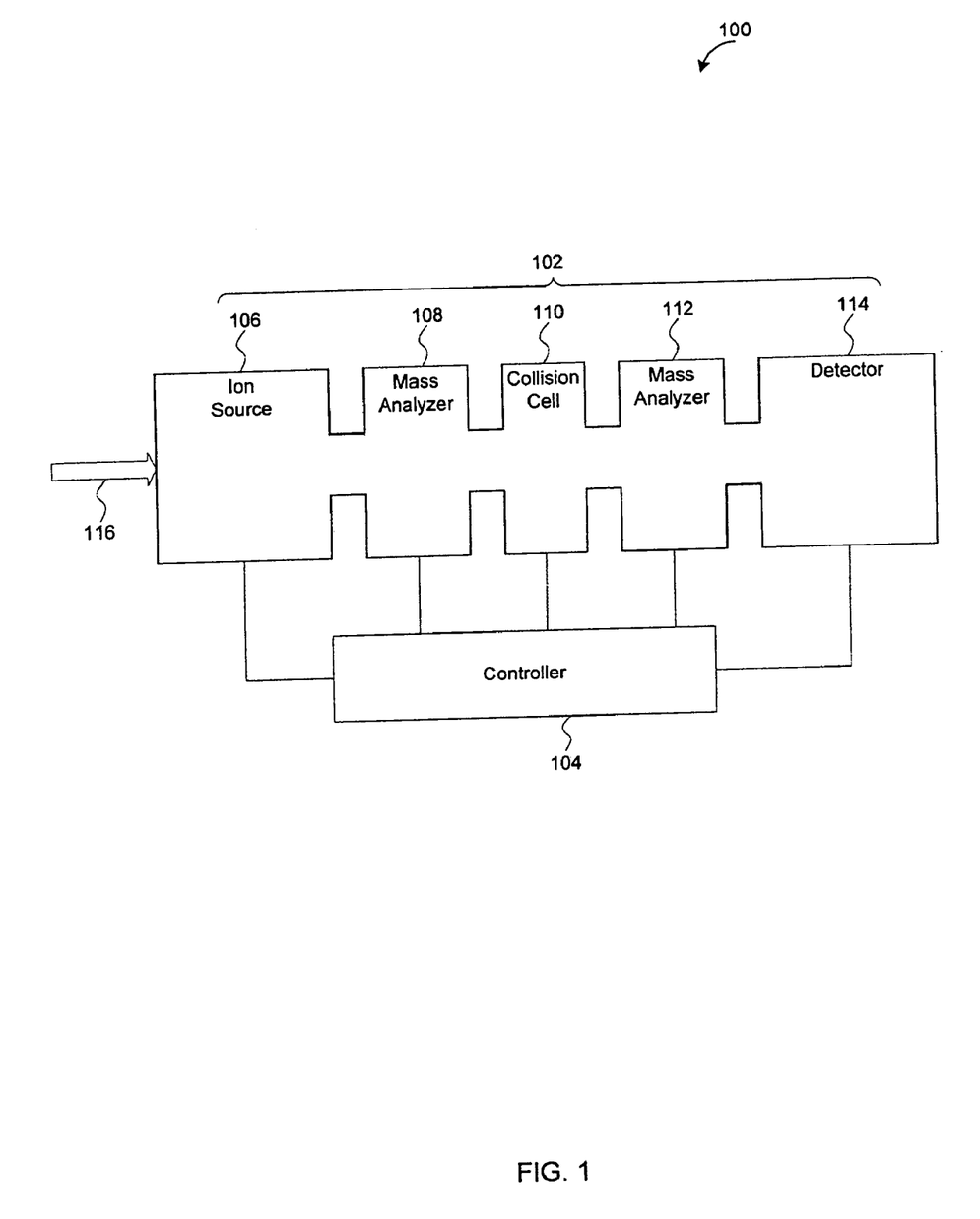
FIG. 1 illustrates a mass spectrometry system implemented in accordance with an embodiment of the invention.

Attention first turns to FIG. 1, which illustrates a mass spectrometry system 100 implemented in accordance with an embodiment of the invention. The mass spectrometry system 100 comprises a mass spectrometer 102, which is implemented as a tandem mass spectrometer. In the illustrated embodiment, the mass spectrometer 102 can operate in a variety of operational modes, depending on a particular type of mass spectrometry experiment to be conducted. For example, the mass spectrometer 102 can operate in a mass spectrometry mode ("MS mode") to acquire a precursor ion spectrum or in a tandem mass spectrometry mode ("MS/MS mode") to acquire a product ion spectrum.

As illustrated in FIG. 1, the mass spectrometer 102 comprises an ion source 106, which operates to produce ions. Depending on a particular operational mode of the mass spectrometer 102, ions that are produced by the ion source 106 can serve as precursor ions, which are fragmented to produce product ions. In the illustrated embodiment, the ion source 106 produces ions using Electrospray Ionization ("ESI"). One benefit of ESI is that it can be readily used in conjunction with a variety of separation procedures, such as HPLC. As illustrated in FIG. 1, the ion source 106 produces ions from analytes present in a sample stream 116. In particular, the sample stream 116 comprises biomolecules that are dispersed in a suitable solvent. For example, the biomolecules can comprise peptides that are produced by subjecting a set of proteins to cleavage or proteolysis. In the illustrated embodiment, the sample stream 116 is introduced into the ion source 106 in a continuous or flowing fashion from a chromatography column (not illustrated in FIG. 1), such as a HPLC column, and successive eluting portions of the sample stream 116 are analyzed by the mass spectrometry system 100 as further described below.

Referring to FIG. 1, the mass spectrometer 102 is implemented in a tandem-in-space fashion and comprises a pair of mass analyzers 108 and 112 and a collision cell 110, which is positioned between the mass analyzers 108 and 112. While two mass analyzers 108 and 112 are illustrated in FIG. 1, it is contemplated that the mass spectrometer 102 can comprise more or fewer mass analyzers for other implementations. For example, it is contemplated that the mass spectrometer 102 can be implemented in a tandem-in-time fashion, in which case the mass spectrometer 102 can comprise a single mass analyzer. As illustrated in FIG. 1, the mass analyzer 108 is positioned downstream with respect to the ion source 106 to receive ions. Depending on a particular operational mode of the mass spectrometer 102, the mass analyzer 108 operates to select ions based on mass-to-charge ratio or to transmit all or substantially all ions. The collision cell 110 is positioned downstream with respect to the mass analyzer 108 to receive ions. Depending on a particular operational mode of the mass spectrometer 102, the collision cell 110 operates to induce fragmentation of ions to produce product ions or to transmit all or substantially all ions. The mass analyzer 112 is positioned downstream with respect to the collision cell 110 to receive ions and operates to separate the ions based on massto-charge ratio. The mass analyzers 108 and 112 can be implemented in a variety of ways, such as using quadrupole mass analyzers, time-of-flight mass analyzers, ion trap mass analyzers, and the like. The collision cell 110 can be implemented in a variety of ways, such as using an inert gas to induce fragmentation of ions based on collisionally induced dissociation.

As illustrated in FIG. 1, the mass spectrometer 102 also comprises a detector 114, which is positioned downstream 0with respect to the mass analyzer 112 to receive ions. The detector 114 operates to detect the abundance of ions to acquire a set of spectra of the sample stream 116. For example, the detector 114 can detect the abundance of precursor ions to acquire a precursor ion spectrum or the abundance of product ions to acquire a product ion spectrum. The detector 114 can be implemented in a variety of ways, such as using an electron multiplier, a scintillation counter, and the like.

Referring to FIG. 1, the mass spectrometry system 100 also comprises a controller 104, which is connected to the mass spectrometer 102 using any wired or wireless transmission channel and operates to control the mass spectrometer 102. In particular, the controller 104 directs the mass spectrometer 102 to operate in a particular operational mode depending on a particular type of mass spectrometry experiment to be conducted. In conjunction with specifying a particular operational mode, the controller 104 can specify or actively change a variety of acquisition parameters for the mass spectrometer 102, such as acquisition parameters for the ion source 106, the mass analyzers 108 and 112, the collision cell 110, and the detector 114. For example, the controller 104 can specify or actively change acquisition parameters to obtain a particular ionization setting, a particular range of mass-to-charge ratios, a particular spectrum acquisition rate, a particular signal-to-noise ratio, a particular mass resolution, a particular fragmentation setting, a particular detector gain, and the like.

As illustrated in FIG. 1, the controller 104 operates as a real-time engine to perform real-time analysis of acquired spectra and to direct the mass spectrometer 102 to operate in a particular operational mode based on results of the real-time analysis. Advantageously, the controller 104 allows automated, data-dependent acquisition of mass spectrometry data by specifying or actively changing a type of mass spectrometry experiment to be conducted based on the results of the real-time analysis. In particular, the results of the real-time analysis can be the basis for initiating or refining additional analysis or for initiating or refining acquisition of additional mass spectrometry data. In such manner, the controller 104 improves the efficiency at which mass spectrometry data can be acquired during a particular chromatography run of the sample stream 116. Such ability of the controller 104 is particularly advantageous in situations where the rate of elution of biomolecules present in the sample stream 116 is too fast for effective manual control of the mass spectrometer 102, where it is undesirable or impractical to interrupt a flow of the sample stream 116, and where there is insufficient material for repeated analysis.

In the illustrated embodiment, the controller 104 performs real-time analysis of acquired spectra based on a set of evaluation criteria. Advantageously, the set of evaluation criteria can be applied in a layered or successive fashion so as to effectively filter out mass spectrometry data that are irrelevant or uninteresting. In such manner, valuable memory resources and processing time can be devoted to mass spectrometry data that are actually relevant or interesting. As a result, the set of evaluation criteria allow for a comprehensive analysis of the sample stream 116 by enhancing acquisition of interesting data while reducing acquisition of uninteresting data. By reducing the amount of uninteresting data to be stored and analyzed, the set of evaluation criteria also assist in accelerating and simplifying identification of biomolecules present in the sample stream 116.

For example, during operation of the mass spectrometry system 100, the controller 104 can direct the mass spectrometer 102 to acquire a precursor ion spectrum of a particular eluting portion of the sample stream 116. Next, the controller 104 can perform a real-time analysis of the precursor ion spectrum based on a first evaluation criterion to determine whether the precursor ion spectrum comprises mass spectrometry data of interest. Based on the real-time analysis of the precursor ion spectrum, the controller 104 can identify a set of peaks of interest and can select the set of peaks for acquisition of additional mass spectrometry data. In particular, the controller 104 can direct the mass spectrometer 102 to acquire a set of product ion spectra for the set of peaks. By performing the analysis of the precursor ion spectrum in real-time, the set of product ion spectra can be acquired from the same eluting portion of the sample stream 116 from which the precursor ion spectrum was acquired, thus allowing a comprehensive analysis of that eluting portion. Next, the controller 104 can perform a real-time analysis of the set of product ion spectra based on a second evaluation criterion to determine whether the set of product ion spectra comprise mass spectrometry data of interest. Based on the real-time analysis of the set of product ion spectra, the controller 104 can identify those product ion spectra that are of interest and can select those product ion spectra for additional analysis. In particular, the controller 104 can analyze those product ion spectra to assign an identification to each of those product ion spectra. Based on such assigned identifications, the controller 104 can also assign an identification to the precursor ion spectrum.

The controller 104 can be implemented in a variety of ways, such as using computer code, hardwired circuitry, or a combination of computer code and hardwired circuitry. It is contemplated that the controller 104 can comprise or can operate in conjunction with a computing device, such as a personal computer, a server computer, a web appliance, a personal digital assistant product, or the like. For example, in connection with performing analysis of spectra based on a particular evaluation criterion, the controller 104 can operate in conjunction with a search engine residing in a personal computer or in a server computer, which can be connected to the controller 104 using any wired or wireless transmission channel. In some instances, the controller 104 can provide a user interface to allow a user to specify a variety of processing options.

Figure 2A:
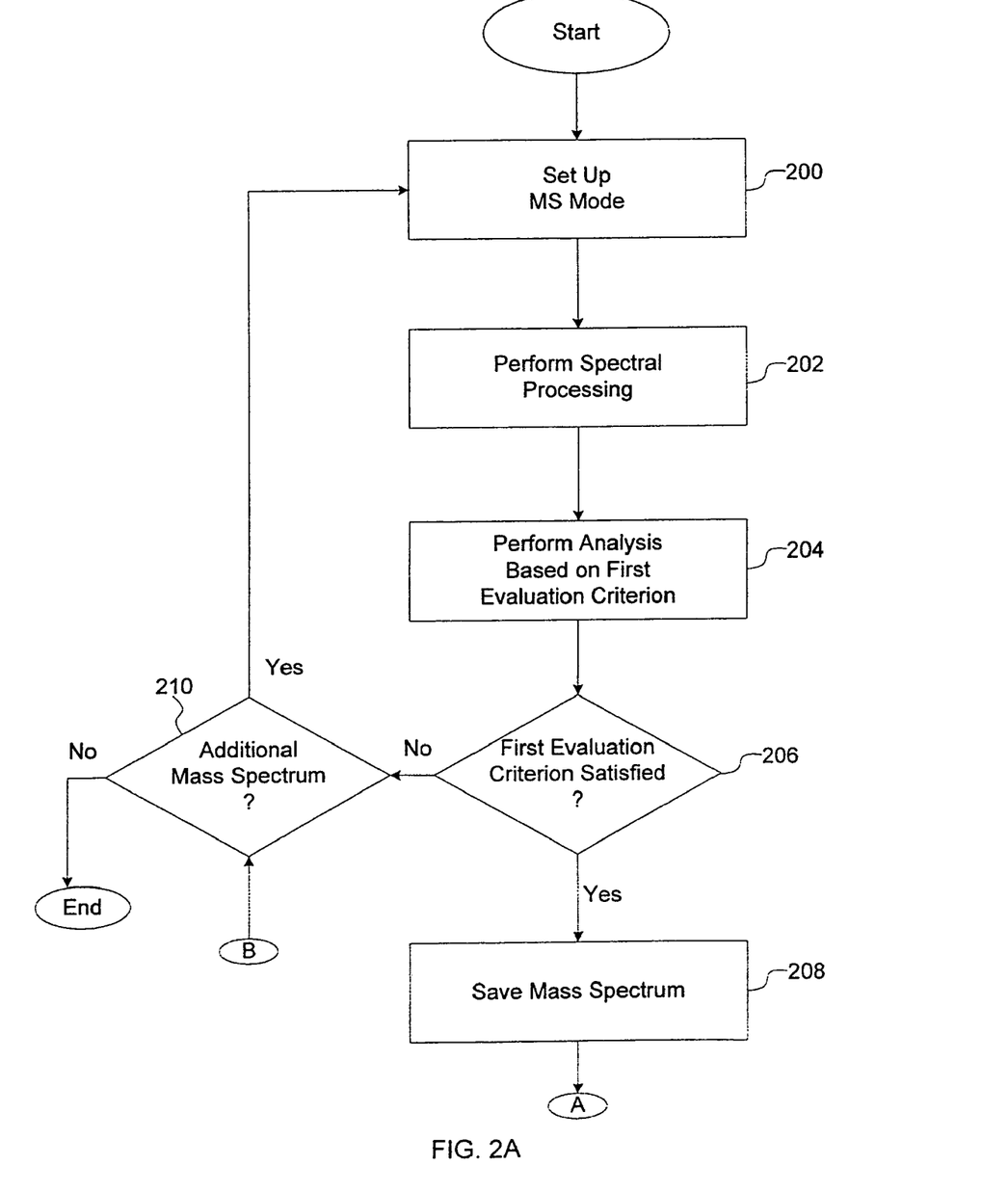
FIG. 2A and FIG. 2B illustrate operations that can performed in accordance with an embodiment of the invention.
Figure 2B:
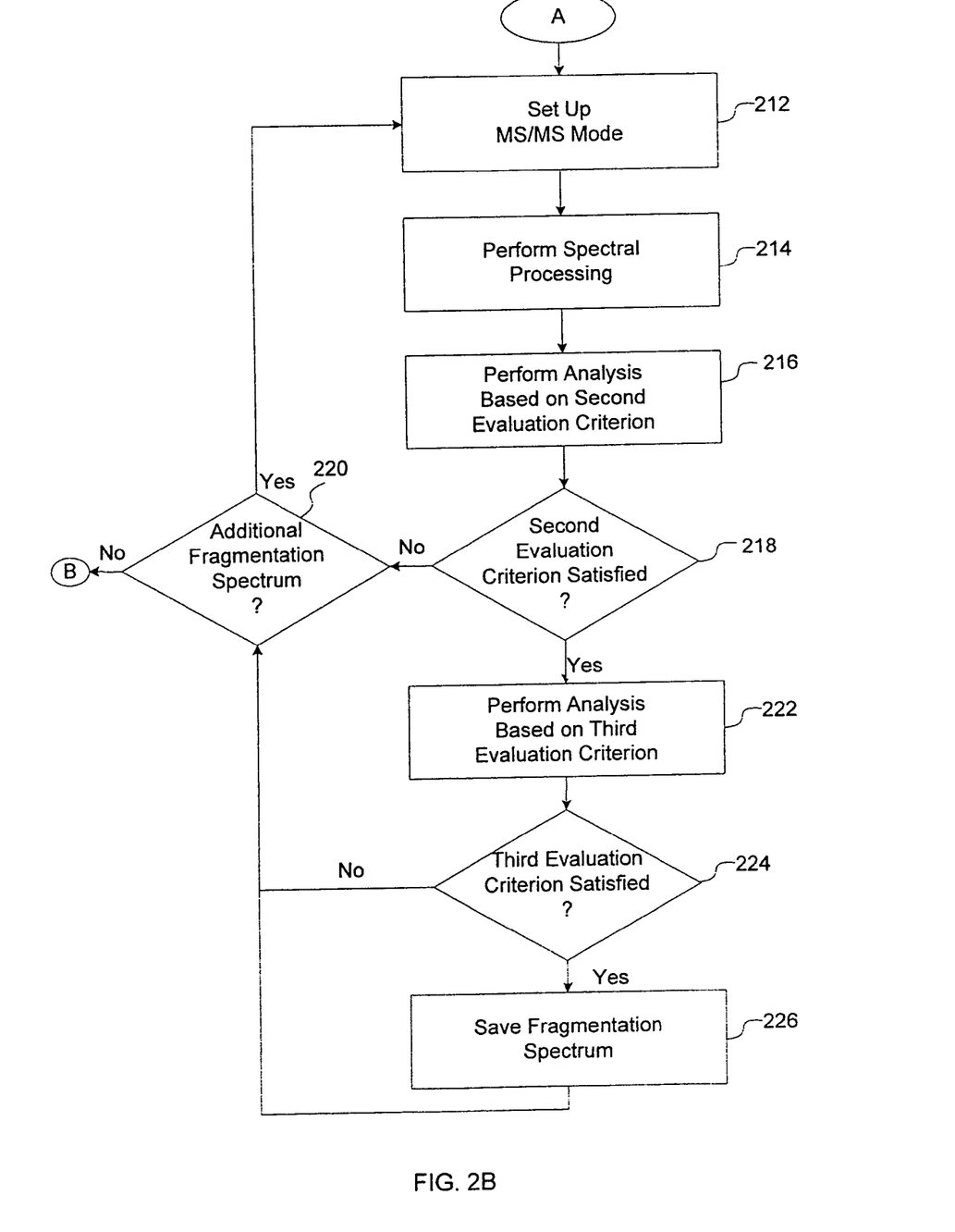

Attention next turns to FIG. 2A and FIG. 2B, which illustrate operations that can be performed in accordance with an embodiment of the invention. In particular, FIG. 2A and FIG. 2B illustrate operations that can be performed by the controller 104 to direct automated, data-dependent acquisition of mass spectrometry data.

With reference to FIG. 2A, the controller 104 initially configures the mass spectrometer 102 to operate in the MS mode (block 200). In the MS mode, the ion source 106 produces ions from biomolecules present in a particular eluting portion of the sample stream 116. In particular, the ion source 106 can produce ions from peptides that are present in that eluting portion. The ion source 106 can also produce ions from other types of biomolecules or from chemical impurities. Next, the mass analyzer 108 and the collision cell 110 transmits all or substantially all of the ions to the mass analyzer 112, which separates the ions based on mass-to-charge ratio. The ions eventually reach the detector 114, which detects the abundance of the ions to acquire a precursor ion spectrum. Depending on the particular format of the precursor ion spectrum, the controller 104 can process the precursor ion spectrum to facilitate additional analysis. As illustrated in FIG. 2A, the precursor ion spectrum is acquired in a raw format, and the controller 104 performs a variety of spectral processing operations on the precursor ion spectrum, such as peak detection, isotopic cluster detection, charge state determination, and the like (block 202). In particular, the controller 104 initially derives a peak list, which comprises peaks that are present in the precursor ion spectrum. Each peak can comprise an intensity value that represents the abundance of ions at a particular mass-to-charge ratio. Next, the controller 104 uses the peak list to detect isotopic clusters that are present in the precursor ion spectrum and then determines a charge state for each of the isotopic clusters.

As illustrated in FIG. 2A, the controller 104 next performs a real-time analysis of the precursor ion spectrum based on a first evaluation criterion to determine whether the precursor ion spectrum comprises mass spectrometry data of interest (block 204). In the illustrated embodiment, the first evaluation criterion is used to determine whether the precursor ion spectrum comprises mass spectrometry data that are peptidic or have a sufficient likelihood of being peptidic. In addition, the first evaluation criterion can impose additional constraints in terms of particular peptidic data of interest. Here, the first evaluation criterion comprises a peptide mass fingerprint score criterion, which is used to determine the degree to which peaks that are present in the precursor ion spectrum match peaks that are present in a set of reference precursor ion spectra. The set of reference precursor ion spectra can comprise experimental or theoretical precursor ion spectra of peptides that are produced by subjecting proteins to cleavage or proteolysis. As illustrated in FIG. 2A, the controller 104 performs a peptide mass fingerprint search for the precursor ion spectrum to derive a set of peptide mass fingerprint scores and then compares the set of peptide mass fingerprint scores with a threshold value, which can be selected or specified by a user. For example, the threshold value can correspond to a minimum level of confidence expressed as a percentage, such as 50%, 60%, 70%, 80%, 90%, or 95%. Each peak present in the precursor ion spectrum that results in a match at or above the threshold value can be identified as being peptidic data of interest or having a sufficient likelihood of being peptidic data of interest. In such manner, the controller 104 can identify a set of peaks of interest and can select the set of peaks for acquisition of a set of product ion spectra. Advantageously, the peptide mass fingerprint search can be accelerated so as to be performed in real-time and, thus, can be referred to as a "rapid" peptide mass fingerprint search. Acceleration of the peptide mass fingerprint search can be achieved since the search need not produce a comprehensive list of possible matches but can simply be used to derive a preliminary indication of which peaks present in the precursor ion spectrum result in a match at or above the threshold value. Thus, the peptide mass fingerprint search need not comprise an exhaustive database search but can be limited in search space. In some instances, the peptide mass fingerprint search can be further accelerated by narrowing the search space in terms of a set of peptides or a set of proteins of interest, which can be selected or specified by a user. It is contemplated that the controller 104 can provide functionality to allow the user to specify particular peptides or particular proteins, such as those comprising particular sequences of amino acids; those comprising amino acids with fixed modifications, such as carbamidomethylation of Cysteines; those comprising amino acids with variable modifications, such as phosphorylation of Serines; those comprising mass differences that are indicative of particular losses, such as phosphate losses; and the like.

It is contemplated that the first evaluation criterion can alternatively, or in conjunction, comprise another type of evaluation criterion to identify a set of peaks of interest. For example, a particular peak can be identified based on its absolute intensity value, its intensity value with respect to intensity values of other peaks, its intensity value with respect to a threshold value, or the like. In particular, it is contemplated that the n most intense peaks present in the precursor ion spectrum can be identified, where n is any integer that can be selected or specified by a user. As another example, a particular peak can be identified based on its membership in an inclusion list or based on its lack of membership in an exclusion list.

As illustrated in FIG. 2A, if the first evaluation criterion is satisfied (block 206), the controller 104 coordinates storage of the precursor ion spectrum in a persistent format, such as in a data file (block 208), and then performs additional operations as further described below. On the other hand, if the first evaluation criterion is not satisfied (block 206), the precursor ion spectrum need not be retained, thus reducing the amount of mass spectrometry data to be persisted. The controller 104 then determines whether any additional precursor ion spectrum is to be acquired (block 210). Such determination can be based on, for example, timing constraints, whether any remaining eluting portion of the sample stream 116 remains to be analyzed, or whether different acquisition parameters should be used. If no additional precursor ion spectrum is to be acquired (block 210), the controller 104 directs the mass spectrometer 102 to proceed to an end configuration. On the other hand, if an additional precursor ion spectrum is to be acquired (block 210), the controller 104 configures the mass spectrometer 102 to operate in the MS mode to acquire the additional precursor ion spectrum from the same or a subsequent eluting portion of the sample stream 116 (block 200). Advantageously, the controller 104 can direct the mass spectrometer 102 to acquire the additional precursor ion spectrum using different acquisition parameters. In such manner, the additional precursor ion spectrum can be acquired from the same elution portion but with improved spectral characteristics. The controller 104 can then process the additional precursor ion spectrum in a similar manner as described above.

With reference to FIG. 2B, the controller 104 next configures the mass spectrometer 102 to operate in the MS/MS mode (block 212). In particular, based on identifying a peak of interest using the first evaluation criterion, the controller 104 directs the mass spectrometer 102 to acquire a product ion spectrum at a mass-to-charge ratio of that peak. It is also contemplated that the mass spectrometer 102 can acquire the product ion spectrum at a range of mass-to-charge ratios that comprise the mass-to-charge ratio of the peak of interest. For example, the range of mass-to-charge ratios can be determined based on an isotopic cluster that comprises the peak of interest. In the MS/MS mode, the ion source 106 produces ions from biomolecules present in a particular eluting portion of the sample stream 116. In particular, the ion source 106 can produce ions from peptides that are present in the same eluting portion of the sample stream 116 from which the precursor ion spectrum was acquired. The ion source 106 can also produce ions from other types of biomolecules or from chemical impurities. Next, the mass analyzer 108 selects a particular ion based on the mass-to-charge ratio of the peak of interest, which ion serves as a precursor ion that undergoes fragmentation in the collision cell 10 to produce product ions. The mass analyzer 112 receives the product ions and separates the product ions based on mass-to-charge ratio. The product ions eventually reach the detector 114, which detects the abundance of the product ions to acquire a product ion spectrum. Depending on the particular format of the product ion spectrum, the controller 104 can process the product ion spectrum to facilitate additional analysis. As illustrated in FIG. 2B, the product ion spectrum is acquired in a raw format, and the controller 104 performs a variety of spectral processing operations on the product ion spectrum, such as peak detection, isotopic cluster detection, charge state determination, and the like (block 214). In particular, the controller 104 initially derives a peak list, which comprises peaks that are present in the product ion spectrum. Each peak can comprise an intensity value that represents the abundance of product ions at a particular mass-to-charge ratio. Next, the controller 104 uses the peak list to detect isotopic clusters that are present in the product ion spectrum and then determines a charge state for each of the isotopic clusters.

As illustrated in FIG. 2B, the controller 104 next performs a real-time analysis of the product ion spectrum based on a second evaluation criterion to determine whether the product ion spectrum comprises mass spectrometry data of interest (block 216). In the illustrated embodiment, the second evaluation criterion is used to determine whether the product ion spectrum comprises mass spectrometry data that are peptidic or have a sufficient likelihood of being peptidic. In addition, the second evaluation criterion can impose additional constraints in terms of particular peptidic data of interest. Here, the second evaluation criterion comprises a sequence tag length criterion, which is used to determine whether peaks that are present in the product ion spectrum are indicative of a sequence tag, namely a sequence of consecutive amino acids that can be present in a peptide or a protein. In particular, the sequence tag length criterion is used to determine whether a series of peaks that are present in the product ion spectrum are indicative of a particular sequence tag length, namely a particular number of consecutive amino acids. As illustrated in FIG. 2B, the controller 104 performs a sequence tag analysis for the product ion spectrum to derive a sequence tag length and compares the sequence tag length with a threshold value, which can be selected or specified by a user. For example, the threshold value can correspond to a minimum sequence tag length and can be any integer that is greater than or equal to 1. If the sequence tag analysis results in a sequence tag length that is the same as or greater than the threshold value, the product ion spectrum can be identified as comprising peptidic data of interest or having a sufficient likelihood of comprising peptidic data of interest. In such manner, the controller 104 can identify the product ion spectrum as being of interest and can select the product ion spectrum for additional analysis as further described below. Advantageously, the sequence tag analysis can be accelerated so as to be performed in real-time and, thus, can be referred to as a "rapid" sequence tag analysis. Acceleration of the sequence tag analysis can be achieved since the analysis need not produce a comprehensive identification of amino acids comprising a sequence tag but can simply be used to derive a preliminary indication of whether peaks that are present in the product ion spectrum are indicative of a sequence tag length at or above the threshold value. Thus, the sequence tag analysis need not comprise a comprehensive sequencing determination but can instead comprise a limited sequencing determination for the purposes of deriving such preliminary indication.

It is contemplated that the second evaluation criterion can alternatively, or in conjunction, comprise another type of evaluation criterion to identify the product ion spectrum as being of interest. For example, the second evaluation criterion can be defined to determine whether the product ion spectrum is indicative of a sequence tag of interest, which can be selected or specified by a user. It is contemplated that the controller 104 can provide functionality to allow the user to specify particular sequence tags, such as those comprising particular sequences of amino acids, those comprising amino acids with fixed modifications, those comprising amino acids with variable modifications, those comprising mass differences that are indicative of particular losses, and the like.

As illustrated in FIG. 2B, if the second evaluation criterion is satisfied (block 218), the controller 104 performs additional operations as further described below. On the other hand, if the second evaluation criterion is not satisfied (block 218), the controller 104 determines whether any additional product ion spectrum is to be acquired (block 220). Such determination can be based on, for example, timing constraints, whether any remaining peaks present in the precursor ion spectrum remain to be analyzed, or whether different acquisition parameters should be used. If no additional product ion spectrum is to be acquired (block 220), the controller 104 determines whether any additional precursor ion spectrum is to be acquired as previously described in connection with FIG. 2A (block 210). On the other hand and with reference to FIG. 2B, if an additional product ion spectrum is to be acquired (block 220), the controller 104 configures the mass spectrometer 102 to operate in the MS/MS mode to acquire the additional product ion spectrum from the same or a subsequent eluting portion of the sample stream 116 (block 212). Advantageously, the controller 104 can direct the mass spectrometer 102 to acquire the additional product ion spectrum using different acquisition parameters. In such manner, the additional product ion spectrum can be acquired from the same elution portion and at the same mass-to-charge ratio but with improved spectral characteristics. The controller 104 can then process the additional product ion spectrum in a similar manner as described above.

With reference to FIG. 2B, the controller 104 next performs an analysis of the product ion spectrum based on a third evaluation criterion to determine whether the product ion spectrum comprises mass spectrometry data of interest (block 222). In the illustrated embodiment, the third evaluation criterion is again used to determine whether the product ion spectrum comprises mass spectrometry data that are peptidic or have a sufficient likelihood of being peptidic. In addition, the third evaluation criterion can impose additional constraints in terms of particular peptidic data of interest. Here, like the second evaluation criterion, the third evaluation criterion comprises a sequence tag length criterion, which is used to determine whether a series of peaks that are present in the product ion spectrum are indicative of a particular sequence tag length. However, the third evaluation criterion can be more stringent in terms of a minimum sequence tag length. As illustrated in FIG. 2B, the controller 104 performs a de novo sequencing analysis for the product ion spectrum to identify amino acids comprising a sequence tag. In connection with performing the de novo sequencing analysis, the controller 104 also derives a sequence tag length and compares the sequence tag length with a threshold value, which can be selected or specified by a user. For example, the threshold value can correspond to a minimum sequence tag length and can be any integer that is greater than or equal to 1. As described above, the third evaluation criterion can be more stringent in terms of the minimum sequence tag length, and, thus, the threshold value specified for the third evaluation criterion can be greater than the threshold value specified for the second evaluation criterion. If the de novo sequencing analysis results in a sequence tag length that is the same as or greater than the threshold value, the product ion spectrum can be identified as comprising peptidic data of interest or having a sufficient likelihood of comprising peptidic data of interest. In such manner, the controller 104 can identify the product ion spectrum as being of interest and can select the product ion spectrum for storage as further described below.

It is contemplated that the third evaluation criterion can alternatively, or in conjunction, comprise another type of evaluation criterion to identify the product ion spectrum as being of interest. For example, the third evaluation criterion can comprise a sequence database score criterion, which is used to determine the degree to which peaks that are present in the product ion spectrum match peaks that are present in a set of reference product ion spectra. The set of reference product ion spectra can comprise experimental or theoretical product ion spectra of peptides that are produced by subjecting proteins to cleavage or proteolysis. In particular, the controller 104 can perform a sequence database search for the product ion spectrum to derive a set of sequence database scores and can then compare the set of sequence database scores with a threshold value, which can be selected or specified by a user. For example, the threshold value can correspond to a minimum level of confidence expressed as a percentage, such as 50%, 60%, 70%, 80%, 90%, or 95%. If the sequence database search results in a match that is at or above the threshold value, the product ion spectrum can be identified as being associated with or having a sufficient likelihood of being associated with a matching peptide or a matching protein. In such manner, the controller 104 can identify the product ion spectrum as being of interest and can select the product ion spectrum for storage. Advantageously, the sequence database search can be accelerated and, thus, can be referred to as a "rapid" sequence database search. In particular, it is contemplated that the sequence database search can be sufficiently accelerated so as to be performed in real-time. Acceleration of the sequence database search can be achieved by narrowing a search space in terms of a set of peptides or a set of proteins of interest, which can be selected or specified by a user. It is contemplated that the controller 104 can provide functionality to allow the user to specify particular peptides or particular proteins, such as those comprising particular sequences of amino acids, those comprising amino acids with fixed modifications, those comprising amino acids with variable modifications, those comprising mass differences that are indicative of particular losses, and the like. In some instances, the sequence database search can be further accelerated by narrowing the search space in terms of a set of peptides or a set of proteins that comprise a sequence tag previously identified in connection with the second evaluation criterion. As another example, the third evaluation criterion can be defined to determine whether the product ion spectrum is indicative of a sequence tag of interest, which can be selected or specified by a user. It is contemplated that the controller 104 can provide functionality to allow the user to specify particular sequence tags, such as those comprising particular sequences of amino acids, those comprising amino acids with fixed modifications, those comprising amino acids with variable modifications, those comprising mass differences that are indicative of particular losses, and the like.

As illustrated in FIG. 2B, if the third evaluation criterion is satisfied (block 224), the controller 104 coordinates storage of the product ion spectrum in a persistent format, such as in a data file (block 226), and then determines whether any additional product ion spectrum is to be acquired (block 220). On the other hand, if the third evaluation criterion is not satisfied (block 224), the product ion spectrum need not be retained, thus reducing the amount of mass spectrometry data to be persisted. The controller 104 then determines whether any additional product ion spectrum is to be acquired (block 220).

EXAMPLE

The following example describes specific aspects of some embodiments of the invention to illustrate and provide a description of those embodiments for one of ordinary skill in the art. The example should not be construed as limiting the invention, as the example merely provides specific methodology useful in understanding and practicing some embodiments of the invention.

The following provides an example of a workflow for automated, data-dependent acquisition of mass spectrometry data:

1) A user defines a first evaluation criterion based on either of, or both, an exclusion list and an inclusion list, which can comprise break-off conditions or thresholds for a set of mass-to-charge ratios.

2) The user defines a second evaluation criterion based on specifying a sequence of amino acids of interest. For example, the user can specify the following using a graphical user interface: [mass-range]:VLESXDIDDLK. Here, the symbol X represents an unknown gap in the specified sequence, and the mass-range indicates a range of mass-to-charge ratios in which the specified sequence (or any fragment thereof) is to be searched. Multiple gaps can also be specified for a sequence of amino acids, such as [10-1200]: VLESXDIX'LK, where X and X' can be the same or different.

Figure 3:
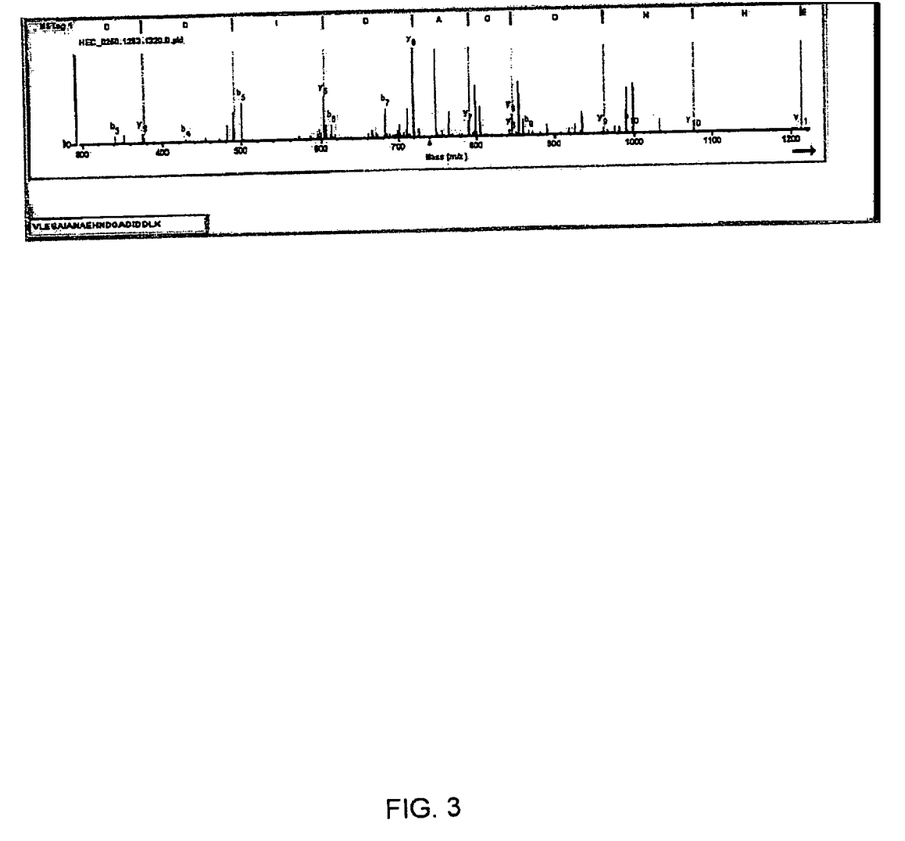
FIG. 3 illustrates a product ion spectrum indicating y- and b-series ions of an identified sequence of amino acids, according to an embodiment of the invention.

3) The user then submits the data-dependent experiment to a real-time engine, which analyzes mass spectrometric data in real-time to identify a sequence of amino acids corresponding to the specified sequence (or any fragment thereof). FIG. 3 illustrates a product ion spectrum indicating y- and b-series ions of such an identified sequence of amino acids, namely VLESAIANAEHNDGADIDDLK.

It should be recognized that the embodiments of the invention described above are provided by way of example, and various other embodiments are encompassed by the invention. For example, with reference to FIG. 1, it is contemplated that the ion source 106 can be implemented to produce ions using another type of ionization process, such as Matrix Assisted Laser Desorption Ionization ("MALDI"), Atmospheric Pressure-Matrix Assisted Laser Desorption Ionization ("AP-MALDI"), or the like. In particular, it is contemplated that certain operations described herein can be advantageously used in connection with MALDI or AP-MALDI to accelerate and to improve the efficiency at which mass spectrometry data can be acquired. As another example, while certain operations have been described as being performed by the controller 104, it is contemplated that these operations can be performed by any real-time engine. Such real-time engine can be implemented in a variety of ways, such as using computer code, hardwired circuitry, or a combination of computer code and hardwired circuitry. As another example, while certain operations have been described as being performed in real-time, it is contemplated that these operations can alternatively, or in conjunction, be performed during post-acquisition processing of mass spectrometry data. As another example, while three evaluation criteria are described with reference to FIG. 2A and FIG. 2B, it is contemplated that more or less evaluation criteria can be used for other implementations. As a further example, while certain operations have been described as being performed with respect to a sample stream, it is contemplated that these operations can be performed with respect to any sample, such as one that is discrete or stationary. In particular, it is contemplated that certain operations described herein can be advantageously used in connection with a discrete or stationary sample to accelerate and to improve the efficiency at which mass spectrometry data can be acquired.

An embodiment of the invention relates to a computer storage product with a computer-readable medium comprising computer code or executable instructions thereon for performing a set of computer-implemented operations. The medium and computer code can be those specially designed and constructed for the purposes of the invention, or they can be of the kind well known and available to those having ordinary skill in the computer software arts. Examples of computer-readable media comprise: magnetic media such as hard disks, floppy disks, and magnetic tape; optical media such as Compact Disc-Read Only Memories ("CD-ROMs") and holographic devices; magneto-optical media such as floptical disks; and hardware devices that are specially configured to store and execute computer code, such as Application-Specific Integrated Circuits ("ASICs"), Programmable Logic Devices ("PLDs"), and Read Only Memory ("ROM") and Random Access Memory ("RAM") devices. Examples of computer code comprise machine code, such as produced by a compiler, and files comprising higher-level code that are executed by a computer using an interpreter. For example, an embodiment of the invention can be implemented using Java, C++, or other programming language and development tools. Additional examples of computer code comprise encrypted code and compressed code. Moreover, an embodiment of the invention can be downloaded as a computer program product, which can be transferred from a remote computer to a requesting computer by way of data signals embodied in a carrier wave or other propagation medium via a transmission channel. Accordingly, as used herein, a carrier wave can be regarded as a computer-readable medium. Another embodiment of the invention can be implemented in hardwired circuitry in place of, or in combination with, computer code.

While the invention has been described with reference to the specific embodiments thereof, it should be understood by those skilled in the art that various changes may be made and equivalents may be substituted without departing from the true spirit and scope of the invention as defined by the appended claims. In addition, many modifications may be made to adapt a particular situation, material, composition of matter, method, operation or operations, to the objective, spirit and scope of the invention. All such modifications are intended to be within the scope of the claims appended hereto. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

We claim:

1. A mass spectrometry system comprising:
    (a) a mass spectrometer; and
    (b) a controller connected to the mass spectrometer including a computer readable medium on which programming is encoded, configured to:
        (i) direct the mass spectrometer to acquire a precursor ion spectrum of a sample stream;
        (ii) analyze, in real-time, the precursor ion spectrum to determine whether a first evaluation criterion is satisfied;
        (iii) if the first evaluation criterion is satisfied, direct the mass spectrometer to acquire a product ion spectrum of the sample stream;
        (iv) analyze, in real-time, the product ion spectrum to determine whether a second evaluation criterion is satisfied; and
        (v) if the second evaluation criterion is satisfied, analyze the product ion spectrum to assign an identification to the product ion spectrum.

2. The mass spectrometry system of claim 1, wherein said controller comprises at least one of computer code, hardwired circuitry or a combination of computer code and hardwired circuitry configured, when evaluating the first evaluation criterion, to determine whether the precursor ion spectrum is indicative of a set of peptides.

3. The mass spectrometry system of claim 1, wherein said controller comprises at least one of computer code, hardwired circuitry or a combination of computer code and hardwired circuitry configured to analyze the precursor ion spectrum in (ii) based on comparing, in real-time, the precursor ion spectrum with a set of reference precursor ion spectra.

4. The mass spectrometry system of claim 1, wherein said controller comprises at least one of computer code, hardwired circuitry or a combination of computer code and hardwired circuitry configured to analyze the precursor ion spectrum in (ii) to select a mass-to-charge ratio at which the product ion spectrum is acquired.

5. The mass spectrometry system of claim 1, wherein the precursor ion spectrum is a first precursor ion spectrum, and said controller comprises at least one of computer code, hardwired circuitry or a combination of computer code and hardwired circuitry configured to, if the first evaluation criterion is not satisfied, direct the mass spectrometer to acquire a second precursor ion spectrum of the sample stream.

6. The mass spectrometry system of claim 1, wherein said controller comprises at least one of computer code, hardwired circuitry or a combination of computer code and hardwired circuitry configured, when evaluating the second evaluation criterion, determine whether the product ion spectrum is indicative of a set of amino acids.

7. The mass spectrometry system of claim 1, wherein said controller comprises at least one of computer code, hardwired circuitry or a combination of computer code and hardwired circuitry configured to analyze the product ion spectrum in (iv) based on performing, in real-time, a first sequencing determination for the product ion spectrum.

8. The mass spectrometry system of claim 7, wherein said controller comprises at least one of computer code, hardwired circuitry or a combination of computer code and hardwired circuitry configured to analyze the product ion spectrum in (v) based on performing a second sequencing determination for the product ion spectrum.

9. The mass spectrometry system of claim 1, wherein said controller comprises at least one of computer code, hardwired circuitry or a combination of computer code and hardwired circuitry configured to analyze the product ion spectrum in (v) based on comparing the product ion spectrum with a set of reference product ion spectra.

10. The mass spectrometry system of claim 1, wherein the product ion spectrum is a first product ion spectrum, and said controller comprises at least one of computer code, hardwired circuitry or a combination of computer code and hardwired circuitry configured to, if the second evaluation criterion is not satisfied, direct the mass spectrometer to acquire a second product ion spectrum of the sample stream.

11. A computer-readable medium comprising executable instructions to:

(a) perform a peptide mass fingerprint search for a precursor ion spectrum to select a set of mass-to-charge ratios associated with the precursor ion spectrum;
(b) direct acquisition of a set of product ion spectra at the set of mass-to-charge ratios;
(c) perform a sequence tag analysis for the set of product ion spectra to derive a sequence tag length for each of the product ion spectra and select at least one of the set of product ion spectra; and
(d) analyze the at least one of the set of product ion spectra to assign an identification to the precursor ion spectrum.

12. The computer-readable medium of claim 11, wherein the executable instructions to perform the peptide mass fingerprint search in (a) comprise executable instructions to identify the set of mass-to-charge ratios as being associated with a set of peptides.

13. The computer-readable medium of claim 11, wherein the executable instructions to perform the peptide mass fingerprint search in (a) comprise executable instructions to compare the precursor ion spectrum with a set of reference precursor ion spectra.

14. The computer-readable medium of claim 11, wherein the executable instructions to perform the sequence tag analysis in (c) comprise executable instructions to identify the at least one of the set of product ion spectra as being associated with multiple, consecutive amino acids.

15. The computer-readable medium of claim 11, wherein the executable instructions to analyze the at least one of the set of product ion spectra in (d) comprise executable instructions to perform a de novo sequencing analysis for the at least one of the set of product ion spectra.

16. The computer-readable medium of claim 11, wherein the executable instructions to analyze the at least one of the set of product ion spectra in (d) comprise executable instructions to perform a sequence database search for the at least one of the set of product ion spectra.

17. A method of operating a mass spectrometry system, comprising:
(a) acquiring a precursor ion spectrum of a sample stream;
(b) analyzing the precursor ion spectrum to determine whether a peptide mass fingerprint score criterion is satisfied; and
(c) if the peptide mass fingerprint score criterion is satisfied, acquiring a product ion spectrum of the sample stream.

18. The method of claim 17, wherein the analyzing the precursor ion spectrum in (b) is performed without interrupting a flow of the sample stream.

19. The method of claim 17, wherein the analyzing the precursor ion spectrum in (b) comprises performing a peptide mass fingerprint search for the precursor ion spectrum to derive a peptide mass fingerprint score and comparing the peptide mass fingerprint score with a threshold value.

20. The method of claim 17, further comprising:
(d) analyzing the product ion spectrum to determine whether a sequence tag length criterion is satisfied; and
(e) if the sequence tag length criterion is satisfied, analyzing the product ion spectrum to assign an identification to the product ion spectrum.

21. The method of claim 20, wherein the analyzing the product ion spectrum in (d) is performed without interrupting a flow of the sample stream.

22. The method of claim 20, wherein the analyzing the product ion spectrum in (d) comprises performing a sequence tag analysis for the product ion spectrum to derive a sequence tag length and comparing the sequence tag length with a threshold value.

23. The method of claim 20, wherein the sequence tag length criterion is a first sequence tag length criterion, and the analyzing the product ion spectrum in (e) comprises:
(i) analyzing the product ion spectrum to determine whether a second sequence tag length criterion is satisfied; and
(ii) if the second sequence tag length criterion is satisfied, coordinating storage of the product ion spectrum.

24. The method of claim 20, wherein the analyzing the product ion spectrum in (e) comprises:
(i) analyzing the product ion spectrum to determine whether a sequence database score criterion is satisfied; and
(ii) if the sequence database score criterion is satisfied, coordinating storage of the product ion spectrum.

* * * * *

UNITED STATES PATENT AND TRADEMARK OFFICE
CERTIFICATE OF CORRECTION

PATENT NO. : 7,498,568 B2
APPLICATION NO. : 11/117874
DATED : March 3, 2009
INVENTOR(S) : Overney et al.

It is certified that error appears in the above-identified patent and that said Letters Patent is hereby corrected as shown below:

Column 13, line 62 (Claim 1, line 5), please delete "configured to:" and insert --and including a processor; and (c) programming configured to be run by said processor, to cause said processor to perform operations comprising:--;
Column 13, line 63 (Claim 1, line 6), please delete "direct" and insert --directing--;
Column 13, line 65 (Claim 1, line 8), please delete "analyze" and insert --analyzing--;
Column 14, line 1 (Claim 1, line 11), please delete "direct" and insert --directing--;
Column 14, line 4 (Claim 1, line 14), please delete "analyze" and insert --analyzing--;
Column 14, line 6 (Claim 1, line 16), please delete "and";
Column 14, line 7 (Claim 1, line 17), please delete "analyze" and insert --analyzing--;
Column 14, line 9 (Claim 1, line 19), please delete "spectrum." and insert --spectrum; and
(vi) if the first evaluation criterion is not satisfied, directing the mass spectrometer to acquire a second precursor ion spectrum from said sample stream.--;
Column 14, line 11 (Claim 2, line 2), delete "controller comprises at least one of computer code, hardwired" and insert --programming is further configured to be run by said processor to evaluate--;
Column 14, line 12 (Claim 2, line 3), delete "circuitry or a combination of computer code and hardwired";
Column 14, line 13 (Claim 2, line 4), delete "circuitry configured, when evaluating";
Column 14, line 17 (Claim 3, line 2), delete "controller comprises at least one of computer code, hardwired" and insert --programming is further configured to be run by said processor to analyze--;
Column 14, line 18 (Claim 3, line 3), delete "circuitry or a combination of computer code and hardwired";
Column 14, line 19 (Claim 3, line 4), delete "circuitry configured to analyze";
Column 14, line 23 (Claim 4, line 2), delete "controller comprises at least one of computer code, hardwired" and insert --programming is further configured to be run by said processor to analyze--;
Column 14, line 24 (Claim 4, line 3), delete "circuitry or a combination of computer code and hardwired";
Column 14, line 25 (Claim 4, line 4), delete "circuitry configured to analyze";
Column 14, line 28 (Claim 5, line 1), delete "wherein the" and insert --wherein said sample stream from which said second precursor ion spectrum is acquired is the same sample stream from which said precursor ion spectrum in (i) was acquired.--;

Signed and Sealed this

Thirteenth Day of July, 2010

David J. Kappos
*Director of the United States Patent and Trademark Office*

CERTIFICATE OF CORRECTION (continued)
U.S. Pat. No. 7,498,568 B2

Column 14, line 29 (Claim 5, line 2), delete "precursor ion spectrum is a first precursor ion spectrum, and";
Column 14, line 30 (Claim 5, line 3), delete "said controller comprises at least one of computer code, hard-";
Column 14, line 31 (Claim 5, line 4), delete "wired circuitry or a combination of computer code and hard-";
Column 14, line 32 (Claim 5, line 5), delete "wired circuitry configured to, if the first evaluation criterion is";
Column 14, line 33 (Claim 5, line 5), delete "not satisfied, direct the mass spectrometer to acquire a second";
Column 14, line 34 (Claim 5, line 6), delete "precursor ion spectrum of the sample stream.";
Column 14, line 36 (Claim 6, line 2), delete "controller comprises at least one of computer code, hardwired" and insert --programming is further configured to be run by said processor to evaluate--;
Column 14, line 37 (Claim 6, line 3), delete "circuitry or a combination of computer code and hardwired";
Column 14, line 38 (Claim 6, line 4), delete "circuitry configured, when evaluating";
Column 14, line 42 (Claim 7, line 2), delete "controller comprises at least one of computer code, hardwired" and insert --programming is further configured to be run by said processor to analyze--;
Column 14, line 43 (Claim 7, line 3), delete "circuitry or a combination of computer code and hardwired";
Column 14, line 44 (Claim 7, line 4), delete "circuitry configured to analyze";
Column 14, line 48 (Claim 8, line 2), delete "controller comprises at least one of computer code, hardwired" and insert --programming is further configured to be run by said processor to analyze--;
Column 14, line 49 (Claim 8, line 3), delete "circuitry or a combination of computer code and hardwired";
Column 14, line 50 (Claim 8, line 4), delete "circuitry configured to analyze";
Column 14, line 54 (Claim 9, line 2), delete "controller comprises at least one of computer code, hardwired" and insert --programming is further configured to be run by said processor to analyze--;
Column 14, line 55 (Claim 9, line 3), delete "circuitry or a combination of computer code and hardwired";
Column 14, line 56 (Claim 9, line 4), delete "circuitry configured to analyze";
Column 14, line 60 (Claim 10, line 2), delete "said" and insert --wherein said programming is further configured to be run by said processor to direct the mass spectrometer to acquire a second product ion spectrum from said sample stream--;
Column 14, line 61 (Claim 10, line 3) delete "controller comprises at least one of computer code, hardwired";
Column 14, line 62 (Claim 10, line 4), delete "circuitry or a combination of computer code and hardwired";
Column 14, line 63 (Claim 10, line 5), delete "circuitry configured to,";
Column 14, line 64 (Claim 10, line 6), delete "satisfied, direct the mass spectrometer to acquire a second" and insert --satisfied.--;
Column 14, line 65 (Claim 10, line 7), delete "product ion spectrum of the sample stream.";
Column 15, line 8 (Claim 11, line 10), after "spectra and" insert --comparing the sequence tag lengths to a threshold sequence tag length having a predetermined sequence tag length, to--;
Column 15, line 42, delete "and"; and
Column 16, line 3 (Claim 17, line 9), delete "stream." and insert --and
(d) if the peptide mass fingerprint score criterion is not satisfied, acquiring a second precursor ion spectrum from said sample stream.--.